United States Patent [19]

Neustadt

[11] 4,230,635

[45] Oct. 28, 1980

[54] SUBSTITUTED 4'-POLYHALOISOPROPYLSULFONANILIDES

[75] Inventor: Bernard R. Neustadt, West Orange, N.J.

[73] Assignee: Schering Corporation, Kenilworth, N.J.

[21] Appl. No.: 933,704

[22] Filed: Aug. 15, 1978

Related U.S. Application Data

[63] Continuation-in-part of Ser. No. 693,446, Jun. 7, 1976, abandoned.

[51] Int. Cl.³ ............................................ C07C 143/74
[52] U.S. Cl. ................... 260/556 A; 71/103; 71/107; 71/111; 424/309; 424/321; 424/322; 260/553 A; 260/556 F; 260/556 AR; 260/556 B; 260/556 S; 260/556 N; 560/28; 560/29; 560/30; 560/33
[58] Field of Search ..................... 260/556 A, 556 F; 71/103

[56] References Cited

U.S. PATENT DOCUMENTS

| | | | |
|---|---|---|---|
| 3,393,993 | 7/1968 | Gilbert et al. | 71/122 |
| 3,396,227 | 8/1968 | Gilbert | 71/122 |
| 3,444,244 | 5/1969 | Newallis et al. | 71/122 |
| 3,468,656 | 9/1969 | Pierpont et al. | 71/122 |
| 3,520,929 | 7/1970 | Maravetz et al. | 71/118 |
| 3,639,474 | 2/1972 | Harrington et al. | 260/556 F |
| 3,661,990 | 5/1972 | Harrington | 260/556 F |
| 3,725,451 | 4/1973 | Tranck et al. | 260/556 F |
| 3,840,597 | 10/1974 | Moore et al. | 71/103 |
| 3,948,987 | 4/1976 | Fridinger | 71/103 |
| 3,996,277 | 12/1976 | Fridinger et al. | 71/103 |

Primary Examiner—Glennon H. Hollrah
Attorney, Agent, or Firm—Barbara L. Renda

[57] ABSTRACT

Disclosed are novel substituted 4'-polyhaloisopropylsulfonanilides which are anti-hypertensive agents useful in the treatment of mammalian hypertension. Additionally, the compounds exhibit herbicidal and fungicidal activity. The compounds are prepared by contacting a 4-polyhaloisopropylaniline with the appropriate substituted-sulfonyl chloride.

18 Claims, No Drawings

SUBSTITUTED 4'-POLYHALOISOPROPYLSULFONANILIDES

This application is a continuation-in-part of my copending application Ser. No. 693,446, filed June 7, 1976, now abandoned.

This invention relates to novel 4'-polyhaloisopropylsulfonanilides which are useful anti-hypertensive agents. Various substituted-sulfonanilides are known in the art; specifically, U.S. Pat. No. 3,920,444 discloses substituted-perfluoroalkylsulfonanilides. However, no anti-hypertensive activity is described for these compounds. More particularly, this invention relates to compounds of the formula:

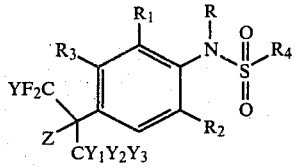

wherein R is hydrogen, lower alkyl, lower alkoxycarbonyl, lower alkylsulfonyl, or a lower alkylcarbamoyl group;

$R_1$ is hydrogen, lower alkyl, lower alkoxy or halogen;

$R_2$ is hydrogen, lower alkyl, lower alkoxy, halogen or lower alkoxycarbonyl;

$R_3$ is hydrogen or lower alkyl, or $R_1$ and $R_3$ together complete an aromatic fused hydrocarbon ring;

$R_4$ is lower alkyl, phenyl, aminophenyl, actamidophenyl, benzyl, di(lower)alkylamino or lower alkylamino;

Y, $Y_1$, $Y_2$ and $Y_3$ are independently hydrogen, chlorine or fluorine; and

Z is hydrogen, chlorine, fluorine or hydroxy.

When the $R_4$ phenyl group is substituted, the substituent may be in the ortho, meta or para position.

The $R_4$ moiety may optionally be substituted by a halogen, a hydroxy or a nitro group, and when $R_4$ is phenyl, may also be substituted by a lower alkyl group. Optionally, the aromatic fused hydrocarbon ring may be hydrogenated to provide a saturated fused hydrocarbon ring.

As used herein, halogen includes fluorine, chlorine, bromine and iodine. Lower alkyl and lower alkoxy denote groups containing from 1 to 7 carbon atoms. Thus, the term lower alkyl includes methyl, ethyl, n-propyl, n-butyl, n-pentyl, n-hexyl and the corresponding branched-chain isomers. Lower alkoxy includes methoxy, ethoxy, n-propoxy, isopropoxy, n-butoxy, isobutoxy, t-butoxy, n-pentoxy and the like. Lower alkylcarbamoyl denotes a group of the formula

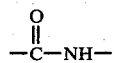

lower alkyl wherein the lower alkyl group contains from 1 to 7 carbon atoms.

Within the scope of formula I there are certain preferential embodiments. $R_3$ is preferably hydrogen. Y, $Y_1$, $Y_2$ and $Y_3$ are preferably all fluorine and Z is preferably hydroxy. A particularly preferred group of compounds are those wherein R is hydrogen and $R_4$ is a methyl group.

The compounds of formula I wherein R is hydrogen or lower alkyl, Z is hydroxy and $R_4$ is other than aminophenyl, are typically prepared by contacting the appropriate 4-polyhaloisopropylaniline of the formula:

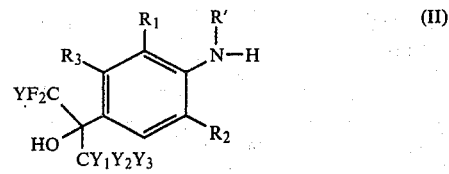

wherein $R_1$, $R_2$, $R_3$, Y, $Y_1$, $Y_2$ and $Y_3$ are as hereinbefore defined and R' is hydrogen or lower alkyl, with a sulfonylchloride of the formula:

wherein $R_4$ is hereinbefore defined (but excepting aminophenyl). This reaction may be conducted using two moles of the aniline or, preferably, in the presence of a weak organic base. Pyridine is the most preferred base for use in this reaction although other bases such as triethylamine may also be utilized.

When the aniline ring is activated by the presence of an ortho electron-withdrawing substituent, e.g. bromine, and R is hydrogen this reaction is preferably conducted at a lower temperature to prevent the formation of the disubstituted sulfonyl derivative. Of course, room temperature or above may be used when the disubstituted derivative is desired.

The compounds wherein $R_4$ is aminophenyl are preparable by base hydrolysis of the corresponding acetamidophenyl compounds. A preferred base for this hydrolysis is sodium hydroxide, but other bases such as potassium hydroxide may also be used.

The compounds wherein R is a lower alkoxycarbonyl group are prepared by reacting the corresponding compound wherein R is hydrogen with the appropriate lower alkyl chloroformate in the presence of a base. In this manner, N-ethoxycarbonyl-4'-(hexafluoro-2-hydroxy-2-propyl)methanesulfonanilide is prepared from 4'-(hexafluoro-2-hydroxy-2-propyl)methanesulfonanilide.

When the compounds wherein R is a lower alkylcarbamoyl group are desired, the corresponding compound wherein R is hydrogen is contacted with the appropriate lower alkyl isocyanate. As an example, 4'-(hexafluoro-2-hydroxy-2-propyl)methanesulfonanilide is converted to 1-ethyl-3-methylsulfonyl-3-[4-(hexafluoro-2-hydroxy-2-propyl)phenyl]urea by this procedure.

The anilines of formula II are produced by methods well known in the art and specifically disclosed in Gilbert, *J. Org. Chem.*, 30, 1001 (1965) and our copending U.S.S.N. 683,104 filed May 4, 1976.

The compounds of formula I wherein Z is chlorine are preparable by contacting the corresponding compound wherein Z is hydroxy with a suitable chlorinating agent, e.g., thionyl chloride. For instance, 4'-(hexafluoro-2-hydroxy-2-propyl)-N-methylmethanesulfonanilide is converted to 4'-(2-chlorohexafluoro-2-propyl)-N-methylmethanesulfonanilide in this manner. The use of a suitable fluorinating agent, e.g., sulfur tetrafluoride, according to the procedure of *J.A.C.S.*, 87, 2410 (1965), affords the analogous compound wherein Z is fluorine, i.e., 4'-(heptafluoro-2-propyl)-N-methylmethanesulfonanilide.

The compounds of formula I wherein Z is hydrogen are obtained by hydrogenation of the corresponding compound wherein Z is chlorine. The use of a catalyst, particularly a catalyst such as palladium on charcoal, facilitates this reaction. Thus, 4'-(hexafluoro-2-chloro-2-propyl)-N-methylmethanesulfonanilide may be converted to 4'-(1,1,1,3,3,3-hexafluoro-2-propyl)-N-methylmethanesulfonanilide by this method.

Certain of the $R_2$ substituents of the compounds of formula I may alternatively be added after the sulfonanilide has been formed by conventional methods. For instance, 4'-(hexafluoro-2-hydroxy-2-propyl)-2'-metylmethanesulfonanilide may be brominated to form 2'-bromo-4'-(hexafluoro-2-hydroxy-2-propyl)-6'-methylmethanesulfonanilide.

The compounds of the present invention have been found to exhibit useful and potent anti-hypertensive activity and are thus useful agents for the treatment of hypertension. Based on laboratory tests, it is considered that the effective dosage (the $ED_{50}$) by oral administration for a compound of the present invention will typically be within the range of 0.5 to 50 mg/kg of mammalian weight. For the preferred compounds 2'-bromo-4'-(hexafluoro-2-hydroxy-2-propyl)-6'-methoxy dimethanesulfonanilide, 2'-bromo-4'-(hexafluoro-2-hydroxy-2-propyl)-6'-methoxymethanesulfonanilide, and 4'-(hexafluoro-2-hydroxy-2-propyl)-2-methoxy-6-methylmethanesulfonanilide, the contemplated human dose is about 1 to 5 mg/kg, administered orally.

The required daily dosage may be administered in single or divided doses. The exact dose to be administered will, of course, be dependent upon where the compound in question lies within the above quoted dosage range and upon the age, weight and drug response of the subject mammal.

The compounds of the present invention are administered orally in the form of a suitable composition. The compositions are thus comprised of an active ingredient and a pharmaceutically acceptable carrier. For oral administration the pharmaceutical carrier may be, for example, either a liquid or a solid. Exemplary of solid carriers are lactose, sucrose, talc, gelatin, agar, pectin, acacia, magnesium stearate, stearic acid and the like. Exemplary of liquid carriers are syrup, peanut oil, olive oil and the like.

A wide variety of pharmaceutical forms may be employed. Thus, if a solid carrier is used, the preparation can be tableted, placed in a hard gelatin capsule in powder or pellet form, or in the form of a troche or lozenge. If a liquid carrier is used, the preparation may be in the form of syrup, emulsion or a soft gelatin capsule.

The pharmaceutical compositions are prepared by conventional techniques such as mixing, granulating and compressing or dissolving the ingredients as appropriate to the desired preparation.

In treating certain patients with the compositions of this invention, it may be desirable to include other pharmaceutically active ingredients in the same dosage unit. For example, in treating patients in whom salt and water retention is a problem, effective amounts of conventional diuretics, e.g., hydrochlorothiazide or trichloromethiazide. Similarly, in treating patients in whom tachycardia might be a problem, an effective amount of a pharmaceutically acceptable beta-blocking agent can be included, e.g., propranolol. The dosage unit could even contain a combination of a compound of this invention, e.g., 2'-bromo-4'-(hexafluoro-2-hydroxy-2-propyl)-6'-methoxymethanesulfanilide, a diuretic, e.g., hydrochlorothiazide, and a beta-blocker, e.g., propranolol.

It is further contemplated that the compounds of the present invention also have herbicidal, insecticidal, fungicidal and other biocidal activity. The compounds have selective and/or broad base activity depending upon the specific compound within formula I and the specific use for which it is applied.

When used as a herbicide, the compounds may be applied to a stand of crops and weeds in the post-emergence treatment and to the ground in the pre-plant or pre-emergence treatment in a number of ways, well known to the art. The water-soluble compounds may be sprayed simply as alcoholic/aqueous solutions. The compounds can be deposited as dusts containing a powdered carrier such as talc, attaclay, etc. The compounds having limited water solubility can be applied as emulsions, the same being formulated as is well known in the art, with commercially available surface-active agents. Among the surface-active agents utilizable are the sulfonated vegetable oils, sodium lauryl sulfate, Tween No. 20 (a polyalkalene ether alcohol), carbowax (polyethylene glycols of M.W. 1500 or more), Atlas G-2122 (polyoxyethylene glycol monolaurate), etc. Penetrants, sequestrants, mineral oils and cosolvents may also be included in the formulations. Typically, the compounds are applied at a rate of 1–10 kg/hectare when used as a herbicide and at a rate of 50–500 ppm when used as a fungicide.

Specifically, 2',5'-dimethyl-4'-(hexafluoro-2-hydroxy-2-propyl)methanesulfonanilide is effective as a herbicide vis-a-vis broad leaf weeds such as *Digitaria adscendens* (crabgrass), *Chenopodium album* (Lamb's quarters) and *Amaranthus lividis* (Pigweed) while inactive vis-a-vis grasses such as *Avena sativa* (Oat) when applied as a pre-emergence herbicide at a rate of 4 kg/hectare. 4'-(Hexafluoro-2-hydroxy-2-propyl)-N-methyl methanesulfonanilide applied at the same rate is similarly effective vis-a-vis broad leaf weeks as well as showing good fungicidal activity against *Phytophthora capsici* (Phytophthora rot) at a rate of 200 ppm.

The following examples describe in detail compounds and compositions illustrative of the present invention. It will be apparent to those skilled in the art that many modifications, both of materials and methods, may be practiced without departing from the purpose and intent of this disclosure.

EXAMPLE 1

4'-(hexafluoro-2-hydroxy-2-propyl)methanesulfonanilide

Add 2.50 g (22 mmole) of methanesulfonyl chloride dropwise to 5.06 g (15 mmole) 4-(hexafluoro-2-hydroxy-2-propyl)-aniline in 25 ml of pyridine and allow to stand overnight. Pour the reaction into $H_2O$ and extract with $Et_2O$. Wash the $Et_2O$ with 1N HCl and extract with 1N NaOH. Acidify the NaOH and extract with $Et_2O$. Dry, concentrate and recrystallize from $Et_2O$-hexane to obtain 4'-(hexafluoro-2-hydroxy-2-propyl)methanesulfonanilide; m.p. 137°–139° C.

EXAMPLE 2

4'-(hexafluoro-2-hydroxy-2-propyl)benzenesulfonanilide

Add 4.22 g (24 mmole) of benzenesulfonyl chloride dropwise to 5.18 g (20 mmole) of 4-(hexafluoro-2-hydroxy-2-propyl)aniline in 25 ml of pyridine and heat to 100° C. for 8 hours. Pour the reaction into $H_2O$ and extract with $Et_2O$. Wash with 1N HCl and extract with 1H NaOH. Acidify the NaOH and extract with $Et_2O$. Dry, concentrate and recrystallize from $Et_2O$ and hexane to obtain 4'-(hexafluoro-2-hydroxy-2-propyl)-benzenesulfonanilide; m.p. 117°–118° C.

EXAMPLE 3

N-[4-(hexafluoro-2-hydroxy-2-propyl)phenyl]-N,N',N'-trimethylsulfamide

To 5.4 g (20 mmole) N-methyl-4-(hexafluoro-2-hydroxy-2-propyl)aniline in 50 ml pyridine add 4.3 g (30 mmole) dimethylsulfamoyl chloride. Stir 16 hours, pour onto water, acidify and extract with $Et_2O$. Wash with 1N NaOH, acidify the aqueous layer, and extract with $Et_2O$. Dry, concentrate and recrystallize first from $CCl_4$, and then from $Et_2O$-hexane to obtain the product; m.p. 63°–65° C.

EXAMPLE 4

N-[4-(hexafluoro-2-hydroxy-2-propyl)phenyl]-N'-ethylsulfamide

To 5.18 g (20 mmole) 4-(hexafluoro-2-hydroxy-2-propyl)aniline and 3.44 g (24 mmole) N-ethylsulfamoyl chloride in 30 ml $CHCl_3$, add 2.18 g (24 mmole) $Et_3N$ in 20 ml $CHCl_3$ and stir for 16 hours. Dilute with $CHCl_3$ and wash with 1N HCl. Dry, concentrate and recrystallize from $Et_2O$-hexane to yield the product; m.p. 178°–179° C.

EXAMPLE 5

4-acetamido-4'-(hexafluoro-2-hydroxy-2-propyl)benzenesulfonanilide

To 8.5 g (36 mmole) 4-(hexafluoro-2-hydroxy-2-propyl)aniline in 30 ml pyridine, add 7.8 g (30 mmole) N-acetylsulfanilyl chloride. Stir 2 hours, pour onto ice and acidify with concentrated HCl. Extract with $Et_2O$, and wash this with 1N NaOH. Acidify the aqueous layer, extract with $Et_2O$ and dry and concentrate. Recrystallize from $Et_2O$-hexane to give the product; m.p. 198°–200° C.

EXAMPLE 6

4-amino-4'-(hexafluoro-2-hydroxy-2-propyl)benzenesulfonanilide

Reflux for 3 hours a solution of 2.3 g (5 mmole) 4-acetamido-4'-(hexafluoro-2-hydroxy-2-propyl)benzenesulfonanilide in 30 ml EtOH and 4 g 50% NaOH. Pour onto water, acidify with concentrated HCl, extract with $Et_2O$, dry and concentrate. Recrystallize from $CHCl_3$-$Et_2O$ to give the product; m.p. 160°–161° C.

EXAMPLE 7

4'-(hexafluoro-2-hydroxy-2-propyl)-2'-methoxy-6'-methylmethanesulfonanilide

To 4.54 g (15 mmole) 4-(hexafluoro-2-hydroxy-2-propyl)-2-methoxy-6-methylaniline in 25 ml pyridine, add 1.94 g (17 mmole) methanesulfonyl chloride. After 16 hours, pour onto 200 ml $H_2O$ and filter the solid. Recrystallize from $Et_2O$-hexane to obtain the product; m.p. 109°–110° C.

EXAMPLE 8

N-[4-(hexafluoro-2-hydroxy-2-propyl)-2-methyl-1-naphthyl]methanesulfonamide

To 3.23 g (10 mmole) 4-(hexafluoro-2-hydroxy-2-propyl)-2-methyl-1-naphthylamine in 25 ml pyridine add 1.25 g (11 mmole) methanesulfonyl chloride. After 2 hours, pour onto water and extract with $Et_2O$. Wash with 1N HCl, and then extract with 1N NaOH. Acidify with concentrated HCl, extract with $Et_2O$, dry and concentrate. Recrystallize from $Et_2O$-hexane to obtain the product; m.p. 174° C.

EXAMPLE 9

4'-(hexafluoro-2-hydroxy-2-propyl)-2'-(methoxycarbonyl)methanesulfonanilide

Add 2.50 g (22 mmole) of methanesulfonyl chloride dropwise to 4.57 g (15 mmole) of methyl 5-(hexafluoro-2-hydroxy-2-propyl)anthranilate in 25 ml of pyridine and allow to stand overnight. Pour the reaction into $H_2O$ and extract with $Et_2O$. Wash the $Et_2O$ with 1N HCl and extract with 1N NaOH. Acidify the NaOH and extract with $Et_2O$. Dry, concentrate and recrystallize from $Et_2O$-hexane to obtain 4'-(hexafluoro-2-hydroxy-2-propyl)-2'-(methoxycarbonyl)methanesulfonanilide; m.p. 147°–148° C.

EXAMPLE 10

N-methanesulfonyl-2'-bromo-4'-hexafluoro-2-hydroxy-2-propyl)-6'-methoxymethanesulfonanilide Add 1.7 g (15 mmole) of methanesulfonyl chloride dropwise to 3.7 g (10 mmole) of 2-bromo-4-(hexafluoro-2-hydroxy-2-propyl)-6-methoxyaniline in 25 ml of pyridine and allow to stand overnight. Pour into $H_2O$ and filter off the solid. Dissolve in $Et_2O$, wash with 1N HCl, dry and concentrate. Recrystallize from MeOH and $H_2O$ to obtain N-methanesulfonyl-2'-bromo-4'-(hexafluoro-2-hydroxy-2-propyl)-6'-methoxymethanesulfonanilide; m.p. 193° C.

EXAMPLE 11

2'-bromo-4'-(hexafluoro-2-hydroxy-2-propyl)-6'-methoxymethanesulfonanilide

Add 2.5 g (22 mmole) of methanesulfonyl chloride dropwise to 5.5 g (15 mmole) of 2-bromo-4-(hexafluoro-2-hydroxy-2-propyl)-6-methoxyaniline in 30 ml of pyridine below 10° C. Allow to stand overnight. Pour into $H_2O$ and decant. Dissolve the oil in $Et_2O$, wash with 1N HCl and extract with 1N NaOH. Acidify the NaOH with HCl and extract with $Et_2O$. Dry and concentrate. Chromatograph the oil on silica gel, eluting with $CHCl_3$. Recrystallize from $CH_2Cl_2$ to obtain 2'-bromo-4'-(hexafluoro-2-hydroxy-2-propyl)-6'-methoxymethanesulfonanilide; m.p. 38°–41° C.

EXAMPLE 12

N-methyl-4'-(1,3-dichlorotetrafluoro-2-propyl)methanesulfonanilide

To 6.1 g (20 mmole) N-methyl-4-(1,3-dichlorotetrafluoro-2-propyl)aniline in 30 ml pyridine add 3.4 g (30 mmole) methanesulfonyl chloride. Stir 1.5 hours, pour onto water, acidify with concentrated HCl and filter. Dissolve the solid in 1N NaOH, wash with Et$_2$O, acidify and filter. Recrystallize the solid from Et$_2$O-hexane to give the product; m.p. 140°–142° C.

EXAMPLE 13

1-ethyl-3-methylsulfonyl-3-[4-(hexafluoro-2-hydroxy-2-propyl)-phenyl]urea

To 3.0 g (23 mmole) AlCl$_3$ in 50 ml nitrobenzene, add 1.4 g (20 mmole) EtNCO. To the solution, add 6.7 g (20 mmole) 4'-(hexafluoro-2-hydroxy-2-propyl)methanesulfonanilide (prepared as in Example 1). Heat for 4 hours at 80° and distill the solvent in vacuo. Triturate the product with 1N HCl and dissolve in Et$_2$O. Dry, concentrate and recrystallize from Et$_2$O-hexane to give the product; m.p. 161°–164° C.

EXAMPLE 14

N-ethoxycarbonyl-4'-(hexafluoro-2-hydroxy-2-propyl)-methanesulfonanilide

To 6.7 g (20 mmole) 4'-(hexafluoro-2-hydroxy-2-propyl)-methanesulfonanilide (prepared as in Example 1) in 100 ml acetonitrile, add 4.1 g (30 mmole) K$_2$CO$_3$ and 2.2 g (20 mmole) ethyl chloroformate. Stir 16 hours, filter and concentrate. Partition the residue between Et$_2$O and 5% Na$_2$CO$_3$. Dry, concentrate and recrystallize first from Et$_2$O-hexane and then from toluene to give the product; m.p. 108°–112° C.

EXAMPLE 15

Repetition of the procedures detailed in the above examples using the appropriate starting materials affords the following compounds of this invention.

4'-(chloro-2-hydroxypentafluoro-2-propyl)benzenesulfonanilide;

4'-(2-hydroxypentafluoro-2-propyl)methanesulfonanilide;

2'-bromo-4'-(2-hydroxy-1,1,3-trichloro-1,3,3-trifluoro-2propyl)-6'-methoxymethanesulfonanilide;

4'-(hexafluoro-2-hydroxy-2-propyl)-N-methylmethanesulfonanilide;

4'-(hexafluoro-2-hydroxy-2-propyl)-α-toluenesulfonanilide;

4'-(1,3-dichloro-2-hydroxytetrafluoro-2-propyl)methanesulfonanilide;

2',6'-dimethyl-4'-(hexafluoro-2-hydroxy-2-propyl)-methanesulfonanilide;

4'-(hexafluoro-2-hydroxy-2-propyl)-N-methylethanesulfonanilide;

2',6'-diethyl-4'-(hexafluoro-2-hydroxy-2-propyl)methanesulfonanilide;

4'-(hexafluoro-2-hydroxy-2-propyl)-N,2',6'-trimethylmethanesulfonanilide;

2',6'-dimethyl-4'-(hexafluoro-2-hydroxy-2-propyl)ethanesulfonanilide;

4'-(hexafluoro-2-hydroxy-2-propyl)-2'-methylmethanesulfonanilide;

2'-bromo-4'-(hexafluoro-2-hydroxy-2-propyl)-6'-methylmethanesulfonanilide;

4'-(hexafluoro-2-hydroxy-2-propyl)-2',6'-diisopropylmethanesulfonanilide;

2'-bromo-4'-(hexafluoro-2-hydroxy-2-propyl)methanesulfonanilide;

4'-(hexafluoro-2-hydroxy-2-propyl)-2'-methoxy-N-methylmethanesulfonanilide;

2',6'-dibromo-4'-(hexafluoro-2-hydroxy-2-propyl)methanesulfonanilide;

4'-(hexafluoro-2-hydroxy-2-propyl)-2',6'-dimethoxymethanesulfonanilide; and

4'-(hexafluoro-2-hydroxy-2-propyl)-2'-methoxymethanesulfonanilide.

EXAMPLE 16

Tablet Formulations

| Formulation I | Milligrams per Tablet |
| --- | --- |
| 2'-bromo-4'-(hexafluoro-2-hydroxy-2-propyl)-6'-methoxymethanesulfonanilide | 50 |
| Lactose, direct compression grade | 173 |
| Microcrystalline cellulose | 30 |
| Sodium lauryl sulfate | 20 |
| Corn starch | 25 |
| Magnesium stearate | 2 |
| | 300 |

Mix together the stated active ingredient, lactose, microcrystalline cellulose, sodium lauryl sulfate and corn starch. Pass through a No. 46 screen. Add magnesium stearate, mix and compress into the desired shape on a tablet machine.

| Formulation II | Milligrams per Tablet |
| --- | --- |
| 2'-bromo-4'-(hexafluoro-2-hydroxy-2-propyl)-6'-methoxymethanesulfonanilide | 50 |
| Lactose, U.S.P. | 191 |
| Dicalcium phosphate | 57 |
| Sodium lauryl sulfate | 20 |
| Polyvinylpyrrolidone | 10 |
| Water 50 ml/1000 tablets | |
| Corn starch | 20 |
| Magnesium stearate | 2 |
| | 350 |

Mix together the stated active ingredient, lactose, dicalcium phosphate and sodium lauryl sulfate. Screen the above mixture through a No. 60 screen and granulate with an aqueous solution containing polyvinylpyrrolidone. Add additional water, if necessary, to bring powders to a pasty mass. Add corn starch and continue mixing until uniform granules are formed. Pass through a No. 10 screen, tray and dry in an oven at 40° C. for 12 to 14 hours. Reduce the dried granulation through a No. 16 screen. Add magnesium stearate, mix and compress into desired shape on a tablet machine.

EXAMPLE 17

Capsule Formulation

| | Milligrams per Capsule |
| --- | --- |
| 2'-bromo-4'-(hexafluoro-2-hydroxy-2-propyl)-6'-methoxymethanesulfonanilide | 50 |
| Lactose, U.S.P. | 173 |
| Microcrystalline Cellulose | 30 |
| Sodium lauryl sulfate | 20 |
| Corn starch | 25 |
| Magnesium stearate | 2 |
| | 300 |

Mix together the stated active ingredient, lactose, microcrystalline cellulose, sodium lauryl sulfate and corn starch. Pass through a No. 80 screen. Add magnesium stearate, mix and encapsulate into the proper size two-piece gelatin capsule.

EXAMPLE 18

Herbicide Formulation 4-acetamido-4'-(hexafluoro-2-hydroxy-2-propyl)benzenesulfonanilide is formulated as an emulsion using Tween No. 20 as a surface-active agent. When applied on the basis of 4 to 8 pounds of compound per acre, this emulsion may be used on a pre-emergence basis against weeds such as barnyard grass, crabgrass and chickweed.

EXAMPLE 19

Herbicide Formulation

2',5'-dimethyl-4'-(hexafluoro-2-hydroxy-2-propyl)-methanesulfonanilide is formulated as an emulsion using Tween No. 20 as a surface-active agent.

What is claimed is:

1. A compound of the formula:

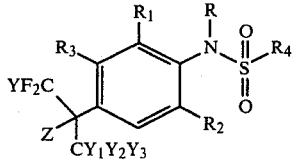

wherein R is hydrogen, lower alkyl, or a lower alkylsulfonyl group;
$R_1$ is hydrogen, lower alkyl, lower alkoxy, or halogen;
$R_2$ is hydrogen, lower alkyl, lower alkoxy, or halogen;
$R_3$ is hydrogen or lower alkyl, or $R_1$ and $R_3$ together complete an aromatic fused hydrocarbon ring;
$R_4$ is lower alkyl;
Y, $Y_1$, $Y_2$, and $Y_3$ are independently hydrogen, chlorine or fluorine; and
Z is hydrogen, chlorine, fluorine, or hydroxy.

2. A compound according to claim 1 wherein Z is a hydroxy group.

3. A compound according to claim 2 wherein Y, $Y_1$, $Y_2$ and $Y_3$ are each independently fluorine or chlorine.

4. A compound according to claim 2 wherein Y, $Y_1$, $Y_2$ and $Y_3$ are each fluorine.

5. A compound according to claim 3 wherein $R_3$ is hydrogen.

6. A compound according to claim 3 wherein R is hydrogen and $R_4$ is methyl.

7. A compound according to claim 3 which is 2',6'-dimethyl-4'-(hexafluoro-2-hydroxy-2-propyl)methanesulfonanilide.

8. A compound according to claim 3 which is 2',6'-diethyl-4'-(hexafluoro-2-hydroxy-2-propyl)methanesulfonanilide.

9. A compound according to claim 3 which is 2'-bromo-4'-(hexafluoro-2-hydroxy-2-propyl)-6'-methylmethanesulfonanilide.

10. A compound according to claim 3 which is 4'-(hexafluoro-2-hydroxy-2-propyl)-2',6'-diisopropylmethanesulfonanilide.

11. A compound according to claim 3 which is 2'-bromo-4'-(hexafluoro-2-hydroxy-2-propyl)methanesulfonanilide.

12. A compound according to claim 3 which is 4'-(hexafluoro-2-hydroxy-2-propyl)-2'-methoxy-6'-methylmethanesulfonanilide.

13. A compound according to claim 3 which is 4'-(hexafluoro-2-hydroxy-2-propyl)-2'-methoxy-N-methylmethanesulfonanilide.

14. A compound according to claim 3 which is 2',6'-dibromo-4'-(hexafluoro-2-hydroxy-2-propyl)methanesulfonanilide.

15. A compound according to claim 3 which is 4'-(hexafluoro-2-hydroxy-2-propyl)-2',6'-dimethoxymethanesulfonanilide.

16. A compound according to claim 3 which is 4'-(hexafluoro-2-hydroxy-2-propyl)-2'-methoxymethanesulfonanilide.

17. A compound according to claim 3 which is N-methanesulfonyl-2'-bromo-4'-(hexafluoro-2-hydroxy-2-propyl)-6'-methoxymethanesulfonanilide.

18. A compound according to claim 3 which is 2'-bromo-4'-(hexafluoro-2-hydroxy-2-propyl)-6'-methoxymethanesulfonanilide.

* * * * *